United States Patent
Croop et al.

(10) Patent No.: US 7,331,785 B2
(45) Date of Patent: Feb. 19, 2008

(54) SELF CLEANING DENTAL MIRROR

(76) Inventors: David Croop, 6391 Turpin Hills Dr., Cincinnati, OH (US) 45244; Don Carter, 4086 Farmwood Ct., Erlanger, KY (US) 41018-2867

( * ) Notice: Subject to any disclaimer, the term of this patent is extended or adjusted under 35 U.S.C. 154(b) by 0 days.

(21) Appl. No.: 10/677,195

(22) Filed: Oct. 2, 2003

(65) Prior Publication Data

US 2005/0074719 A1    Apr. 7, 2005

(51) Int. Cl.
*A61C 1/00*    (2006.01)
(52) U.S. Cl. ....................................... 433/31
(58) Field of Classification Search ................. 433/30, 433/31, 82, 85; 359/509, 845, 882; 600/247; 606/18.19
See application file for complete search history.

(56) References Cited

U.S. PATENT DOCUMENTS

| | | | |
|---|---|---|---|
| 1,905,633 A | | 4/1933 | Feltham |
| 2,984,009 A | * | 5/1961 | Codoni ........................ 433/30 |
| 2,984,909 A | * | 5/1961 | Johnston ...................... 433/30 |
| 3,001,288 A | * | 9/1961 | Freedman .................... 433/31 |
| 3,014,279 A | | 12/1961 | Fosdal |
| 3,048,924 A | * | 8/1962 | Whitman et al. ............. 433/30 |
| 3,164,904 A | * | 1/1965 | Barnes ......................... 433/30 |
| 3,250,005 A | * | 5/1966 | White .......................... 433/85 |
| 3,342,178 A | * | 9/1967 | Freedman ............... 128/200.21 |
| 3,640,304 A | * | 2/1972 | Fox et al. ............... 137/315.11 |
| 3,849,889 A | | 11/1974 | Rosander |
| 3,969,824 A | | 7/1976 | Widen et al. |
| 3,986,266 A | * | 10/1976 | Vellender ..................... 433/30 |
| 4,408,991 A | | 10/1983 | Engel |
| 5,045,055 A | * | 9/1991 | Gonser et al. ................ 604/33 |
| 5,139,420 A | * | 8/1992 | Walker ......................... 433/31 |
| 5,139,421 A | | 8/1992 | Verderber |
| 5,295,826 A | | 3/1994 | Yandell et al. |
| 5,385,468 A | | 1/1995 | Verderber |
| 5,457,611 A | | 10/1995 | Verderber |
| 5,654,824 A | | 8/1997 | Tarr |
| 5,827,059 A | | 10/1998 | Nykaza |
| 5,851,112 A | | 12/1998 | Daikuzono |
| 5,951,284 A | * | 9/1999 | Lake ............................ 433/31 |
| 6,247,924 B1 | | 6/2001 | Gunnarson |
| 2003/0091956 A1 | | 5/2003 | Chadwick |

* cited by examiner

*Primary Examiner*—Cris Rodriguez
*Assistant Examiner*—Sunil K. Singh
(74) *Attorney, Agent, or Firm*—R. Christian Macke

(57) ABSTRACT

A self cleaning dental mirror having air orifices and water orifices integrated into the handle to clean the reflective surface. An air valve and a water valve are positioned within the handle and are operated by depressing appropriately positioned pushbuttons. The reflective surface itself is removable from the handle and replaceable. Alignment provisions between the reflective surface and handle insure that the reflective surface is properly positioned relative to the handle so that the air orifice and water orifice are directed at the reflective surface. A quick disconnect allows the self cleaning dental mirror to be readily connected and disconnected to air and water supply lines. The self cleaning dental mirror and all of its components are autoclavible.

11 Claims, 6 Drawing Sheets

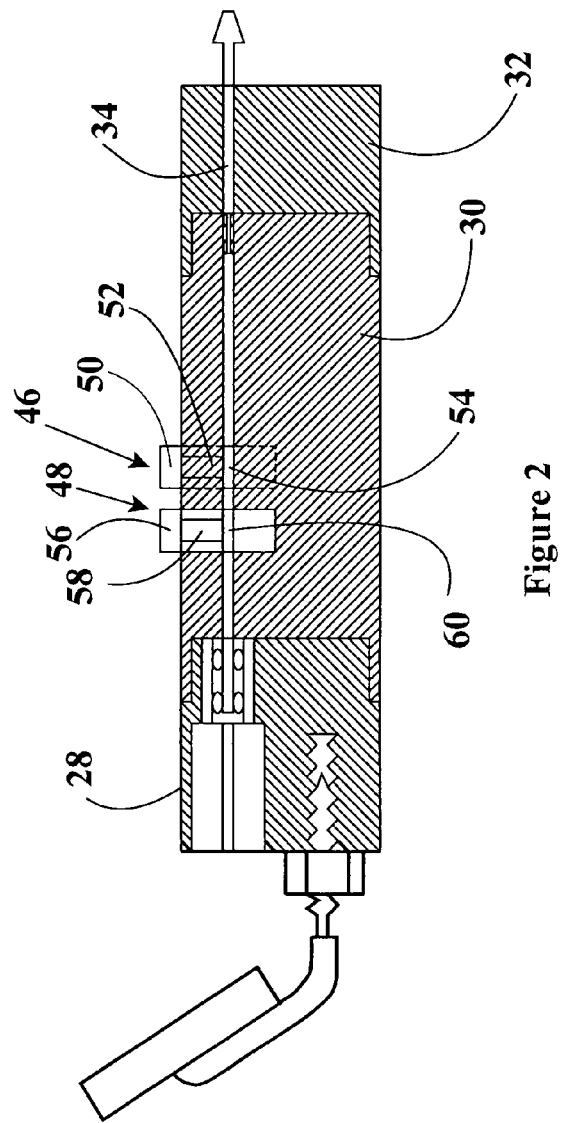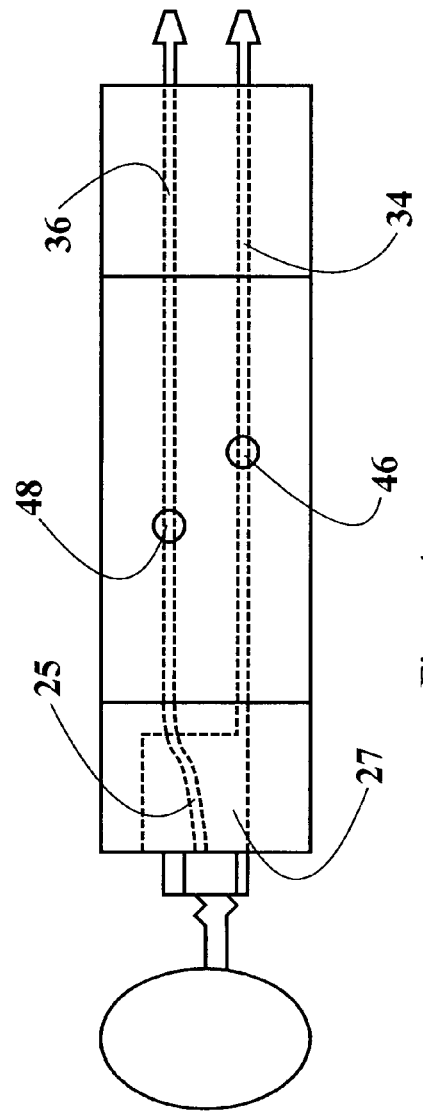

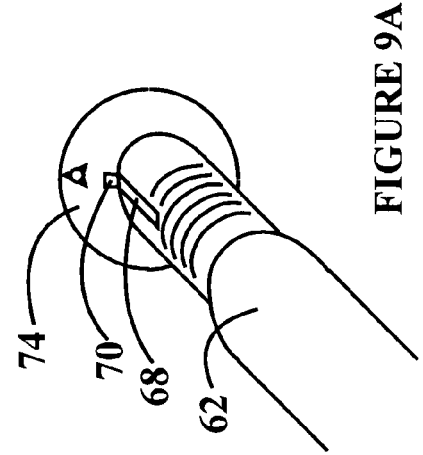
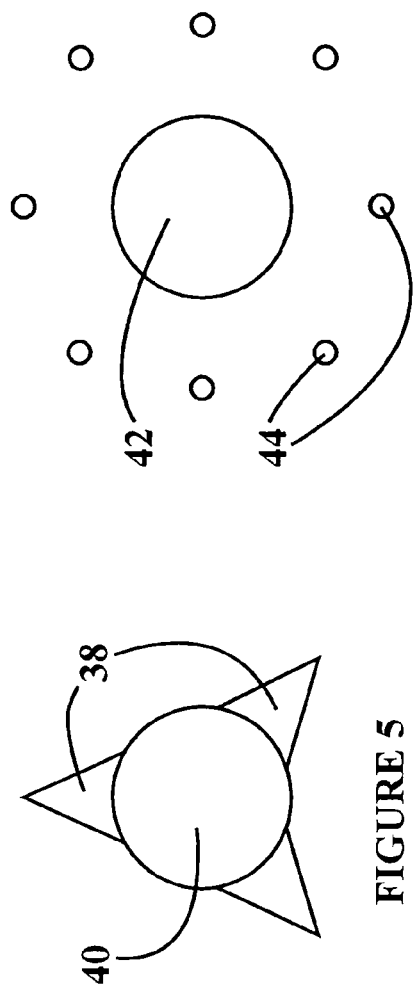
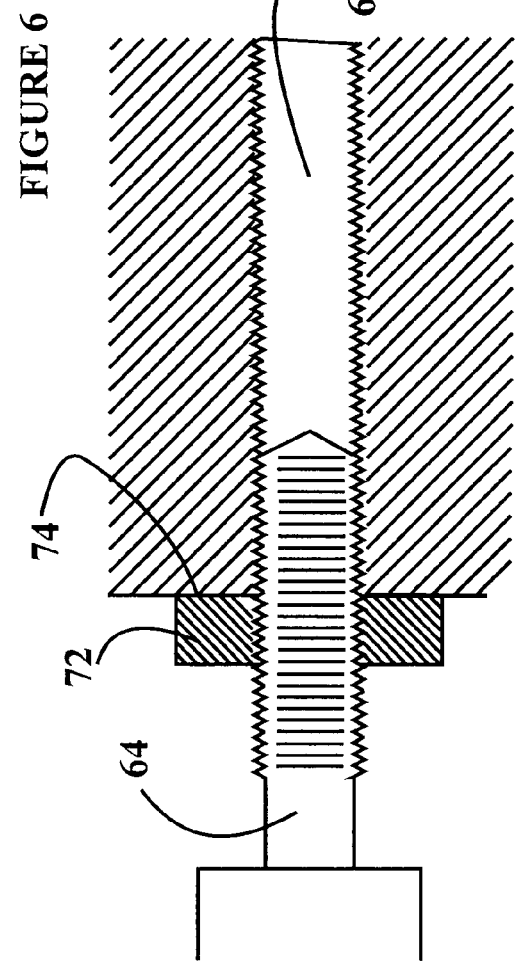

SELF CLEANING DENTAL MIRROR

FIELD OF THE INVENTION

This invention relates to an improved dental mirror having self cleaning provisions.

BACKGROUND OF THE INVENTION

One of the most important tools in the dentist's arsenal is the handheld mirror that is utilized in virtually every procedure to give the dentist a complete view of the inside of the patient's mouth. Handheld mirrors generally comprise a small circular piece of reflective glass held in a frame and affixed at an angle to an elongated handle, where it is held by the dentist or other dental professional performing a procedure.

A well known problem associated with the dental mirror is that the mirror frequently becomes covered with debris such that the dentist's view is obstructed. The dentist is then required to withdraw the mirror from the patient's mount, clean the mirror, place the mirror back in the patient's mouth, get re-oriented and resume the procedure. In procedures in which a rotary drilling, sanding or polishing device is used, the problem of debris accumulating on the mirror is particularly acute because, in addition to the fragments that break away from the patient's teeth and gums and land on the mirror, water spray is also present during the use of a high speed drill from water that is used to cool and lubricate the drilling site. The accumulation of debris and water droplets from the cooling spray, as well as saliva and the patient's breath fogging the mirror, all present the well-known problem of obscured mirror vision for the dentist.

While the steps of withdrawing the mirror from the patient's mouth, wiping it clean, re-inserting the mirror (which requires re-orientation by the dentist and re-acquiring his "target") may be only a few seconds for experienced dentists, when those steps must be repeated 50 to 100 times in the course of a normal day, the cumulative effect is significant. That is, even if the withdrawal of the mirror, wiping it clean, re-inserting it and re-orienting the tool and mirror take only 10-15 seconds, the cumulative effect, if it must be done 100 times per day, will be an additional 1,500 seconds, or more than 25 minutes. In addition, the repetitive wiping of the mirror is a source of aggravation and additional stress to the dentist. Often, though, the delay can be much greater, depending on the inexperience or lack of skill of the dentist or of the location of the procedure in the patient's mouth. That is, if the procedure is toward the rear on the inside of the teeth, the dentist will rely heavily on his mirror. If he must get re-oriented every time he removes, wipes and re-inserts the mirror, the procedure becomes significantly longer. The problem is so significant that many dentists, particularly those experienced and skilled enough to be able to "feel" the procedure even when their visibility is impaired, will resist the mirror withdrawal, wiping, re-insertion and re-orientation, depending on the kind of procedure and the status of the procedure when the vision is obscured. If, for instance, the visibility in the mirror becomes obstructed near the end of a particular step in the procedure, the dentist often will complete the step with impaired vision rather than take the time to remove the mirror to wipe it clean.

Insofar as the problem is well known, a number of prior art solutions have been attempted to eradicate or reduce the mirror withdrawal, wiping and re-insertion by the dentist. As will be discussed in more detail herein, all of the prior art solutions have disadvantages that are eliminated by the present invention. U.S. Pat. No. 5,654,824 includes a rotary wiper blade that engages the mirror surface to wipe away debris and liquid thereon. However, the '824 wiper blade itself partially obscures the dentist's vision, and it will still require withdrawal from the patient's mouth and wiping, or else being sprayed with a water syringe operated by a dental assistant to completely expel the debris from the mirror. U.S. Pat. No. 5,827,059 also includes a wiper blade that is manually pushed across the mirror surface to accumulate and discard debris and liquid that has collected on the mirror. Besides the disadvantage of still requiring air or water to expel the accumulated debris and water after the use of the wiper, the use of the wiper blade requires a significant distance of travel for the dentist's thumb on thumb member 11 to perform a full wipe. To utilize the '059 patented apparatus the dentist will have to disengage from the procedure, push the thumb member up and back down to execute a wipe, and then re-engage the procedure, so the same basic problem will persist in that significant time will be added to procedures to clean the mirror.

U.S. Pat. No. 4,408,991 discloses a dental mirror having a bulbous end under the mirror itself in which a rotary device is housed. In that manner, a dentist can spin the mirror to eject debris and liquid accumulated thereon without removing the mirror from the patient's mouth. U.S. Pat. No. 6,247,947 provides a similar rotary mirror. Both rely upon the centripetal force imparted to the debris by the mirror to eject it from the reflective surface, so debris accumulated near the middle of the mirror may not be ejected. In addition, the inclusion of the rotary device makes the end of the mirror large and cumbersome and difficult to handle, all problems when working in the small confines of the human mouth with other instrumentation.

U.S. Pat. Nos. 3,164,904; 3,014,279; 1,905,633; 3,849,889; and 3,986,266 all provide dental mirrors having either air or water or both to be applied across the mirror surface to blow debris and liquid off the reflective surface. In those patented arrangements, a number of disadvantages are apparent. The use of remote solenoid valves or other external valving by several of the devices will result in the addition of a large piece of costly equipment, and a self contained air source, that will eat up space in the examination room.

In addition to the mechanical solutions, a more human response would be, and has been, to have a dental assistant watch the procedure and, when the mirror's visibility is impaired, use an air and water syringe to dispel the accumulated debris thereon. However, the ability for an assistant to perform such function is difficult to perfect and still is imperfect because the dentist and dental assistant will have different views of the mirror and because the application of air and water must be coordinated with the work being done by the dentist without obstructing the operator's view. In addition, the use of dental assistants to keep the mirror clean is labor intensive and costly. The preferable solution is to put the control into the hands of the dentist or auxiliary personnel in a way that reduces or eliminates the time spent keeping the mirror clean and the delays resulting therefrom.

While the prior art solutions recognize the attendant problems of debris covered mirrors and resulting obstructed visibility, necessitating frequent withdrawal of the mirror, wiping the mirror clean, reinserting the mirror in the patient's mouth, and reorientation by the dentist, there are a number of shortcomings with the prior art solutions. The design and positioning on a mirror instrument of air orifices and water orifices relative to each other, as well as to the reflective surface, will be critical to achieve optimum water dispersion across the reflective surface. The distance from the air orifices and water orifices to the reflective surface is particularly important and is addressed by the present invention. None of the prior art devices address those problems. In addition, legal requirements pertaining to the sterilization of dental instruments require that a mirror, or any other instrument, must be autoclavable, or able to withstand high pressure (up to 30 PSI), high temperature (up to 274° F.) sterilization. The present mirror, and all components thereof, have been designed with that in mind. The prior art devices came before the legal requirements were in place, so they obviously did not address them. In fact, a frequent source of failures of existing mirrors is the scratching or chipping of the reflective surface that occurs during autoclaving the mirror.

While the mirror is one of the most important tools that a dentist has, the simple ordinary mirror on an elongated handle is relatively inexpensive and frequently replaced. In the prior art devices providing self cleaning mirrors, there is no provision for removal or replacement of the reflective surface only. In addition to cracking and chipping that occur during autoclaving, mirrors are frequently scratched, cracked or chipped when they come in contact with high speed rotary devices such as drills, which they are routinely right next to during a procedure. Thus, in the common event of damage, cracking or chipping of the mirror, with prior art self cleaning mirrors the entire device would have to be discarded. While it is inexpensive and commonplace to replace simple mirrors, replacement cost becomes an issue when the mirror handle incorporates air and water orifices; the investment in such a device mandates that it not be so readily discarded. Repair of the unit would be preferred, so self cleaning mirrors that include provisions to repair and replace only the items most likely to fail, such as the reflective surface or pushbutton valves, would be preferred since most of the investment in the instrument is not lost. None of the prior art recognizes the need to make the reflective surface replaceable, as the present invention does. By making it replaceable, in light of the need to have the mirror properly positioned to be in line with the air and water jets, provisions must be made to ensure that the replacement reflective surface is properly positioned. The position of the reflective surface is also important insofar as it must line up with the pushbuttons located on the handle so that the instrument can be properly held by the dentist. Because none of the prior art devices contemplated replacement of the mirror, none of them considered or contemplated the need to have provisions ensuring the replacement mirror lined up with the air and water orifices, or with the operator pushbuttons.

In designing the handle having valves controlling air and water valves therein, for ease of manufacture of the handle it is necessary that the valves be linearly offset. The pushbuttons that control air flow and water flow in the present invention are not aligned, but rather are intentionally offset so that the air and water channels in the instrument, specifically in the valve body section and tail section thereof, may be formed and utilized using simple pushbutton valve controls.

Finally, the dental mirror of the present invention is necessarily designed with provisions for attaching air and water supply lines thereto, as are many prior art devices. The present invention, in addressing the need to frequently disconnect and clean the mirror, has a quick disconnect device that allows the instrument to be quickly and simply attached and detached to the air and water lines.

OBJECTS OF THE INVENTION

It is an object of the present invention to provide a dental mirror having provisions for self cleaning the reflective surface without interrupting a dental procedure being performed.

It is another object of the present invention to provide a self cleaning dental mirror having a removable and replaceable reflective surface.

It is yet another object of the present invention to provide a self cleaning mirror having field removable and replaceable pushbuttons and valves controlling air and water orifices positioned within the handle.

It is a further object of the present invention to provide a self cleaning mirror having pushbuttons and valves controlling air and water orifices positioned within the handle to allow operator immediate accessibility while being linearly offset to simplify manufacturing of the handle.

It is a further object of the present invention to provide a self cleaning dental mirror having air and water lines incorporated therein such that either or both are precisely directed at the reflective surface.

It is yet another object of the present invention to provide a self cleaning dental mirror having superior water dispersion characteristics provided by surrounding at least one water jet with multiple air jets.

It is a further object of the present invention to provide a self cleaning dental mirror having a replaceable reflective surface and alignment provisions ensuring that the air and water jets are properly directed at the reflective surface.

It is another object of the present invention to provide a self cleaning dental mirror having a replaceable reflective surface and alignment provisions ensuring that the reflective surface is visible to the dentist when his/her thumb is positioned on the pushbutton valves controlling air and water.

It is yet another object of the present invention to provide a self cleaning dental mirror that reduces the need for the dentist to withdraw the mirror from a patient's mouth to wipe the mirror clean.

It is another object of the present invention to provide a dental mirror having a quick disconnect means.

It is a further object of the present invention to provide a dental mirror having air and water connections to the handle thereof that provides means for cutting off air and water flow upon disconnection from the air and water supply lines.

These and other objects and advantages of the present invention will be apparent from a review of the following specification and accompanying drawings.

SUMMARY OF THE INVENTION

The present invention is a self-cleaning dental mirror comprising an elongated handle and a reflective surface affixed to one end of the handle. Means for communicating air and water through the handle to air and water orifices which direct air and water at the reflective surface are provided. An air valve means and a water valve means are positioned within the handle and control air flow to the air orifices and water flow to the water orifices. In a significant feature of the present invention, the self-cleaning dental mirror and all of its components are constructed from materials that are autoclavable, capable of withstanding sterilization through high temperature and high pressure. In the most preferred embodiment of the invention, the handle and all other metal parts are constructed from anodized aluminum, while the O-rings providing seals around pipe connections are formed from VITON™.

The self cleaning dental mirror of the present invention has provisions for connecting an air supply hose and a water supply hose which, in the most preferred embodiment, comprises a quick disconnect coupling having air nipple and water nipple connections positioned near the end of the elongated handle opposite the reflective surface. The quick disconnect coupling further comprises a simple and quick means for engaging and disengaging the mirror and handle to the air supply hose and water supply hose. The quick disconnect coupling further provides means for cutting off flow from said air supply hose and said water supply hose upon disengagement of the mirror and handle.

The reflective surface of the self cleaning dental mirror is mounted on an angled arm and shank and removably attached to the elongated handle. A number of alternative cooperating means for removing and replacing the reflective surface are provided between the mirror and the handle so that the mirror can be replaced without replacing the other parts or components. One means for removing and replacing the reflective surface is provided by a hexagonal shank extending from the mirror that is received by a hexagonal sleeve in the handle. A recess in the hexagonal shank allows insertion of a locking device, such as an Allen screw, spring loaded bearing or locking collet fingers, to prevent longitudinal translation of the shank within the sleeve. Rotational translation is prevented as a result of the hexagonal shank in the hexagonal sleeve. It is specifically contemplated that the use of other shapes (triangular, square, pentagonal, etc.) may also be used for the shape of the shank and sleeve without departing from the principles of the present invention. Another alternative means for removing and replacing the reflective surface is provided by mounting alignment pins on a cylindrical shank extending from the reflective surface, and providing slots in the handle for receiving the alignment pins. Another alternative means for removing and replacing the reflective surface that is simple and quick to employ comprises an exteriorly threaded screw and an interiorly threaded sleeve for receiving the screw. In light of the necessity that the reflective surface is properly positioned so that the air and water jets are directed at it, a means for aligning the threaded screw within the interiorly threaded sleeve to achieve the proper position for the reflective surface is provided. A notch on the threaded screw is aligned with a notch on the handle to ensure proper positioning of the reflective surface. Once aligned, a locking means is applied to hold the reflective surface in its properly aligned position relative to the handle and air and water orifices. All of the various alternative means for removing and replacing the reflective surface thus provide a shank extending from the reflective surface that is received in a sleeve formed in the handle. All further include provisions for insuring that the reflective surface is aligned with the air and water jets, and for preventing longitudinal or rotational translation of the shank within the sleeve.

The self cleaning dental mirror of the present invention also incorporates an arrangement for the air jets and water orifices to enhance the dispersion of the water across the reflective surface. Specifically, in the most preferred embodiment at least one water jet is encircled by air jets so that water emitted from the water jet is interrupted by air jets from all directions, resulting in the desired dispersion.

The air valve means and water valve means, positioned in the elongated handle, are placed such that an operator can easily and comfortably keep one thumb on both of the pushbuttons controlling the valves while holding the mirror in a normal fashion. The mirror alignment provisions are also applied such that the reflective surface is visible to the dentist while his thumb is properly positioned on the pushbuttons. Within the handle, however, the valves and pushbuttons are linearly offset so that the air channel and water channel, formed therein to communicate air and water to the air jets and water jets, do not overlap.

BRIEF DESCRIPTION OF THE DRAWINGS

FIG. 2 is a front partially sectioned view of the self cleaning dental mirror of the present invention.

FIG. 4 is a top view of the self cleaning dental mirror of the present invention.

FIG. 5 is a detail view of the preferred embodiment of the relative arrangement of the water orifices and air orifices in the elongated handle of the present invention.

FIG. 6 is an alternative embodiment of the relative arrangement of the water orifices and air orifices in the elongated handle of the present invention.

FIG. 8 is a detail view depicting the quick disconnect means between the reflective surface and the elongated handle of the present invention.

FIG. 9A is a detail view depicting the alignment provisions comprising a threaded shank and sleeve and locking nut ensuring proper positioning of the reflective surface relative to the elongated handle and air and water orifices.

DETAILED DESCRIPTION OF THE INVENTION

Figure 1:
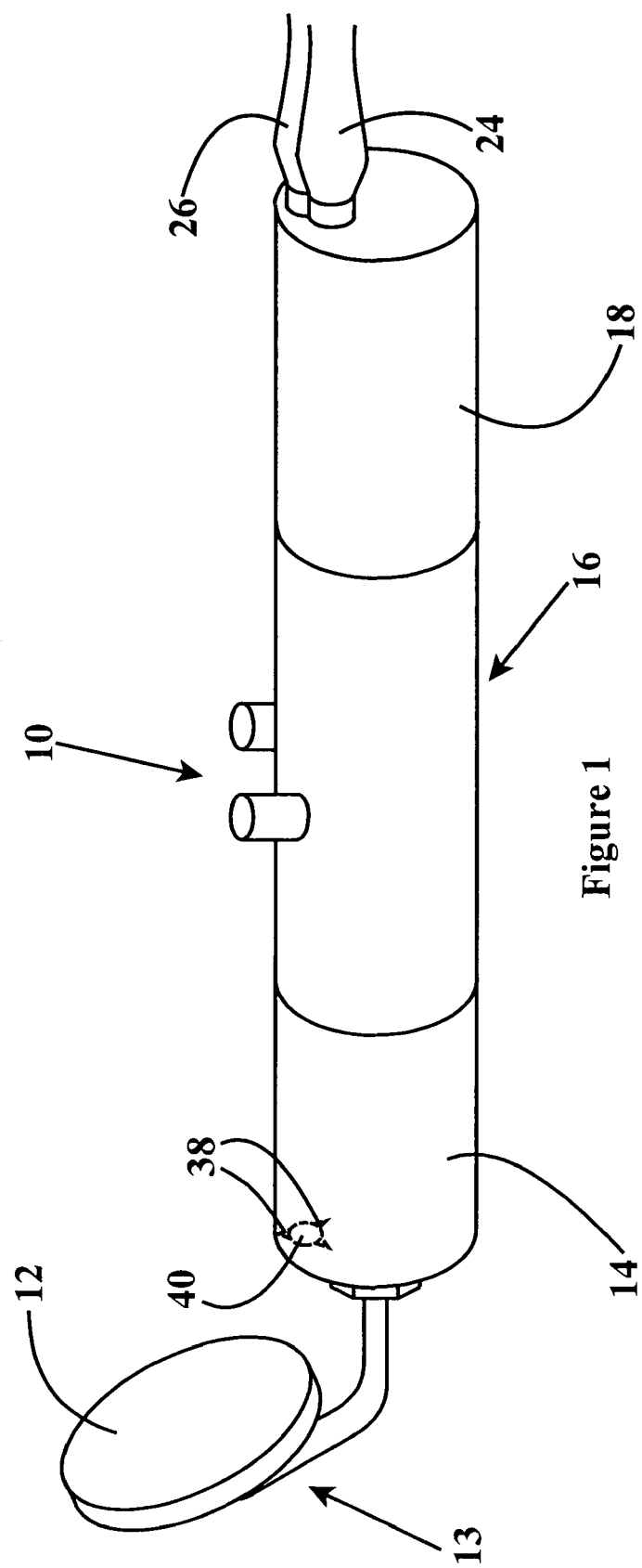
FIG. 1 is a perspective view of the self cleaning dental mirror of the present invention.

The present invention comprises a dental mirror 10 having a reflective surface 12 as part of a removable and replaceable mirror head 13. The mirror head 13 is affixed to a distal end 14 of an elongated handle 16, as shown in FIG. 1. In the most preferred embodiment of the present invention, at the opposed end 18 of the handle 16 there is an attached air line nipple 20 and water line nipple 22 (see FIGS. 2 and 3). As shown in FIG. 1 while in use, an air line 24 and water line 26 are connected to the elongated handle 16.

Figure 3:
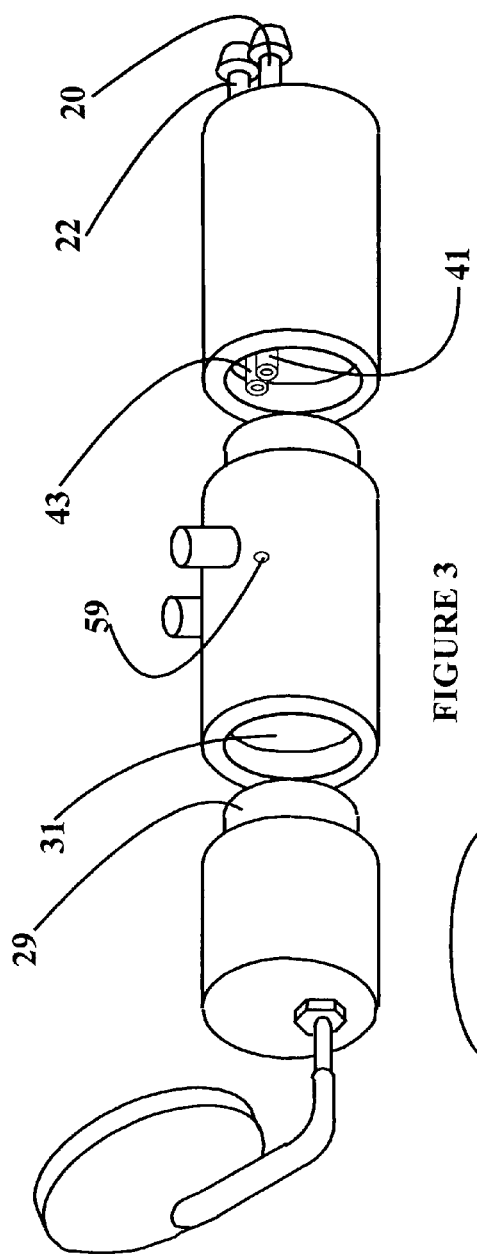
FIG. 3 is a disassembled view of the self cleaning dental mirror of the present invention.

In the most preferred embodiment of the present invention, the elongated handle 16 is constructed from three distinct pieces, a head section 28, a valve body section 30, and a tail section 32. As shown in FIGS. 2 and 3, the head section 28, valve body section 30 and tail section 32 are assembled such that means for communicating air and water through the handle 16, an air channel 34 and water channel 36, are aligned and extend the length of the valve body section 30 and tail section 32. At the connection between the valve body section 30 and the head section 28, the air line and water line become concentric with a water pipe 25 positioned within a larger diameter air channel 27 formed in the head section 28. The concentric arrangement of the water and air provide a means for dispersing water expelled from water orifice 40. In this way, air flow and water flow extend the length of the handle 16 from the air nipple 20 and water nipple 22 to the air orifices 38 and water orifice 40 formed in the front face 74 of the handle 16.

Figure 7:
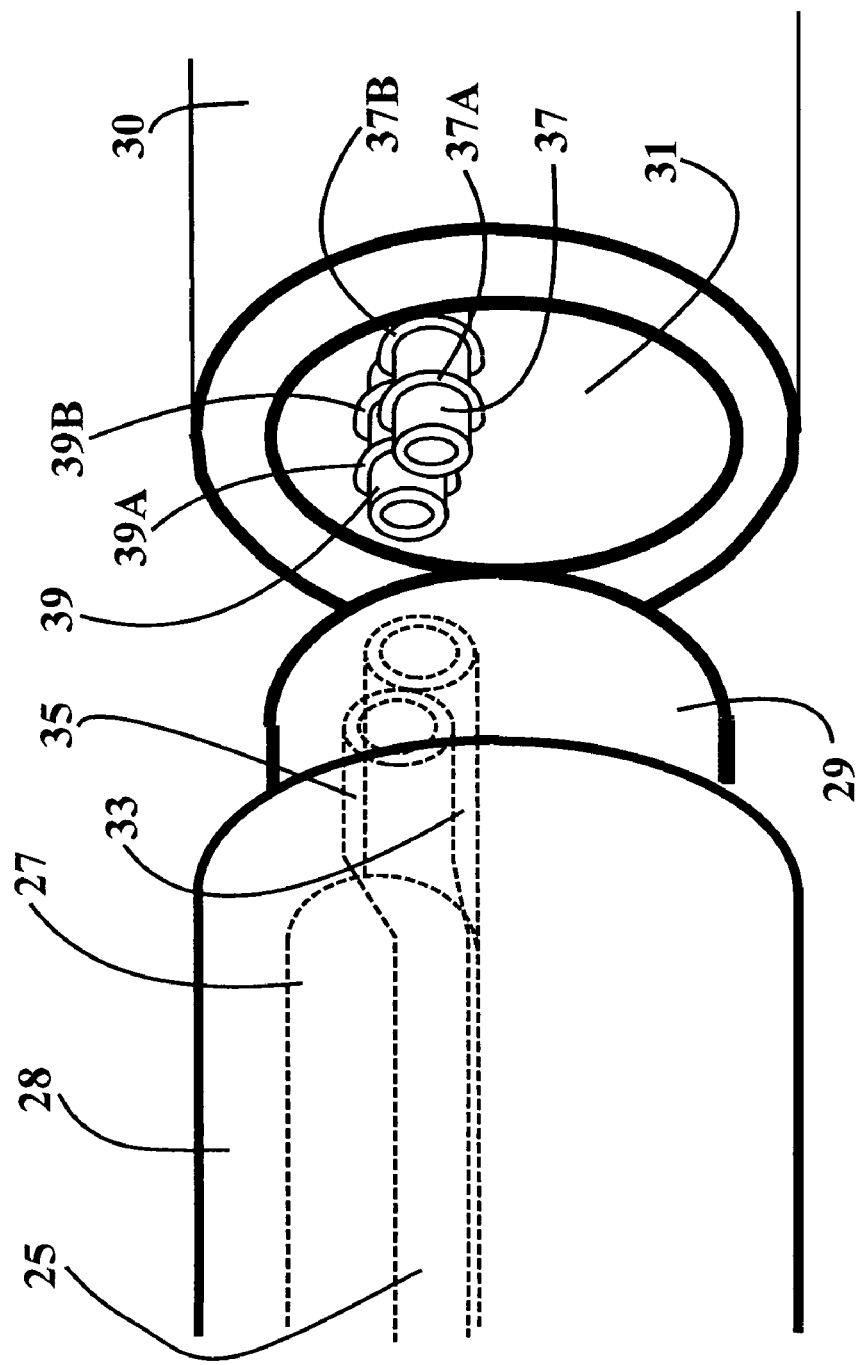
FIG. 7 is a detail view of the quick disconnect couplings between the head section and valve body section, and between the valve body section and tail section.

The head section 28 fits into the valve body section 30 with a male extension 29 from the head section 28 being received in a female cavity 31 formed in the valve body section 30, as shown in FIGS. 3 and 7. Within the male extension 29 there are an air pipe female extension 33 and a water pipe female extension 35, as shown in FIG. 7. When the head section 28 and valve body section 30 are properly assembled, the air pipe female extension 33 engages an air pipe male extension 37, and the water pipe female extension 35 engages a water pipe male extension 39, as shown in FIG. 7. The male extension 29 and female cavity 31 are keyed to that they only fit together if the air pipe female extension 33 and water pipe female extension 35 line up with the air pipe male extension 37 and water pipe male extension 39. To insure that the pipe connections are air tight and water tight, the air pipe male extension 37 has double O-rings 37A, 37B, and the water pipe male extension 39 has double O-rings 39A, 39B as shown in FIG. 7. In order that the self cleaning dental mirror 10 of the present invention be autoclavible, it is contemplated that the O-rings be constructed of VITON™, although other flexible materials having sealing capabilities that would withstand high temperature, high pressure sterilization may be used without departing from the principles of the present invention. The inclusion of a male extension 29 and female cavity 31 between the head section 28 and valve body section 30 provides a means for quickly disconnecting both ends of the valve body section 30, allowing only that portion of the dental mirror to be repaired or replaced. This is a significant feature of the present invention because it allows a user to easily replace a portion of the dental mirror 10 without having to send it out for repair or replacement.

Between the valve body section 30 and the tail section 32 there is a means for quickly disconnecting the tail section 32 from the rest of the dental mirror 10 so that the instrument may be easily and quickly transported from room to room without requiring any tube or pipe connections. The means for quickly disconnecting the tail section 32 from the rest of the dental mirror includes provisions for cutting off the flow of water and air so that, when the tail section 32 is disengaged from the valve body section 30, air and water are cut off and do not flow out of the air pipe extension 41 or water pipe extension 43 extending from the tail section 32. This air and water cut off may be performed by any of various means, including electrical circuit permissives or mechanical interlocks (not shown).

While the most preferred embodiment shows the water orifice 40 surrounded triangularly by air orifices 38, other alternative designs in which the water jets are surrounded by air jets are specifically contemplated and do not depart from the principles of the present invention. One alternative example is shown in FIG. 5 wherein the water jet 42 is surrounded by a ring of air jets 44. The preferred embodiment of the present invention contemplates that air jets surrounding a water jet will create beneficial dispersion of the water, advantageous for the purpose of emitting water fully and evenly across the reflective surface 12. Pushbutton air valves 46, 48 provide means for an operator to separately control the valves, thereby allowing precise titration of the air and water, or providing only air or only water as necessary to clean and/or dry a mirror surface to maintain visibility of the surgical site.

Figure 11:
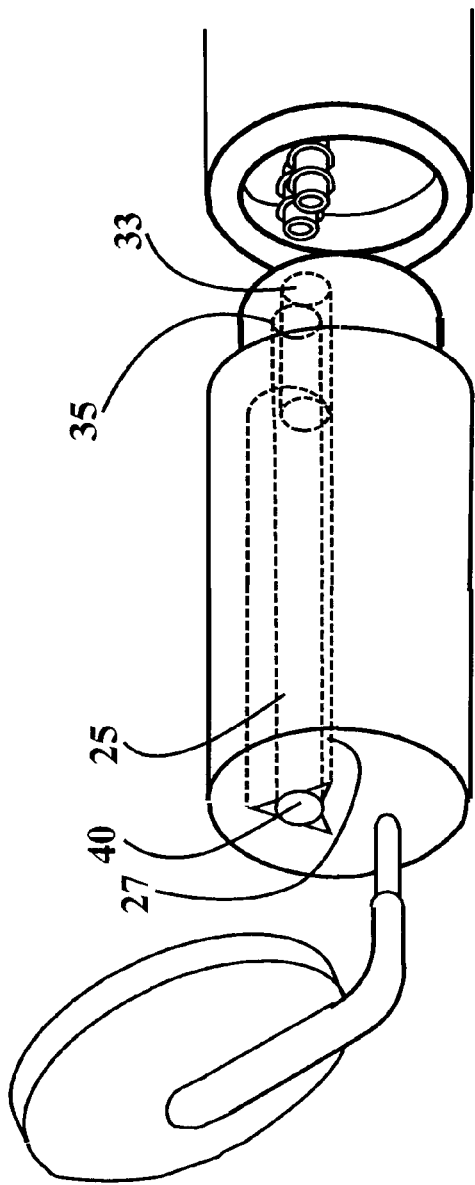
FIG. 11 is a detail view of the couplings between the air and water that convert them from being parallel to concentric.

In the most preferred embodiment of the present invention, the head section 28 of the handle 16 is provided with a water pipe 25 through which water is communicated from the water pipe female extension 35 at one end to the water orifice 40 at the other end (see FIG. 11). Air is communicated in the head section 28 from an air pipe female extension 33 into a larger diameter air channel 27, as shown in FIGS. 4, 7, and 11. This water-pipe-within-an-air-channel arrangement provides a means for atomizing the water output at water orifice 40, which improves the cleansing capacity of the water by outputting water in pressure bursts.

Figure 10:
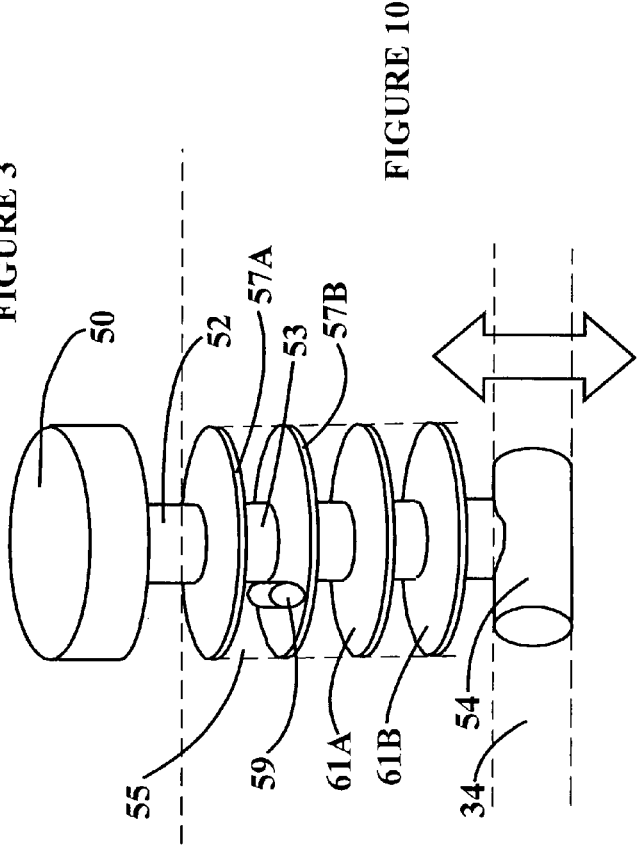
FIG. 10 is a detail view of the removable and replaceable pushbuttons.

The valve body section 30 of the present invention is designed with a pushbutton air valve 46 and a pushbutton water valve 48 incorporated therein as shown in FIGS. 2 and 3. The pushbutton air valve 46 comprises a spring loaded head 50 extending above the surface of the valve section 30. The head 50 is connected by a shaft 52 through a sleeve 53 to a plunger 54, as shown in FIG. 10. The shaft 52 moves through the sleeve 53, in the direction indicated in FIG. 10. When the head 50 is not depressed, the spring loaded plunger 54 seals off the air channel 34 and prevents the flow of air through it. The shaft 52 and sleeve 53 are mounted in a cylindrical bore 55 formed in the valve body section 30, as shown in FIG. 10. The sleeve 53 has two spaced rings 57A, 57B formed thereon such that, when the shaft 52 and sleeve 53 are seated within the cylindrical bore 55, a retaining pin 59, inserted in valve body section 30 (see FIG. 3) holds the shaft 52 and sleeve 53 in position. Removal of retaining pin 53 allows the entire pushbutton valve assembly 46 to be removed and replaced. Gasketing O-rings 61A, 61B insure a water tight and air tight seal around the valve assembly, as shown in FIG. 10. When pushbutton head 50 is depressed, the plunger 54 is pushed out of the air channel 34, allowing air to flow along the length of the handle 16 to be emitted at air orifices 38. Similarly, the pushbutton water valve 48 comprises a head 56, a shaft 58 and a plunger 60. When head 56 is depressed, water flows through water channel 36 along the length of the handle 16 to be emitted at water jet 40. The pushbutton air valve 46 and pushbutton water valve 48 are integrated into the handle 16 as shown in FIG. 3 so that they are accessible to a user's thumb while also being linearly offset so that the air channel 34 and water channel 36 do not overlap. The pushbutton air valve 46 and pushbutton water valve 48 are positioned on the handle 16 relative to the reflective surface 12 such that, when held by a user, the user's thumb naturally engages the pushbutton valves 46, 48 when the reflective surface 12 is positioned to give the user a view inside a patient's mouth.

The mirror head 13 is removably connected to the elongated handle 16 through an angled arm 62. In a significant feature of the present invention, the mirror head 13 is provided with a means for quickly disconnecting the mirror head 13 from the handle 16 and replacing it. The means for quickly disconnecting the mirror head 13 allows a user to replace only that component without having to replace or repair the entire instrument. This is beneficial because cracking or chipping of the reflective surface 12 is the most common source of failure of dental mirrors, and because it will be dramatically less expensive to replace just the reflective surface 12 mounted on the angled arm 62 than to replace the entire device 10. A user's investment in the device 10 will be significantly greater than that of a standard dental mirror that must be repeatedly extracted from a patient's mount and wiped clean, but the bulk of the cost of the engineering and production that will be borne by the user will be protected because the handle 16, with all the valving, control, machining and pipe connections, will not be discarded if or when the reflective surface 12 fails. The mirror head 13 is simply disconnected and a new one put in its place.

To ensure that a replacement head 13 is correctly and stably installed to the handle 16, the present invention provides means for retaining the mirror head 13 in the handle 16 that prevent rotational or longitudinal translation. Once installed, the retention means holds the mirror head 13 such that the reflective surface 12 is the proper lineal distance from the water orifice 40 and air orifices 38. In the most preferred embodiment, the lineal distance will be 10 to 35 millimeters.

The self cleaning dental mirror of the present invention is also provided with means for aligning the reflective surface 12 with the pushbuttons 46, 48 such that the reflective surface 12 is oriented properly to allow a user holding the handle 16 with his thumb comfortably positioned on the valve pushbuttons 46, 48 to have a view of the reflective surface 12.

In a preferred embodiment of the present invention, the retaining means is provided by a male exteriorly threaded screw 64 extending from the end of the angled arm 62 opposite the reflective surface 12 (see FIGS. 8 and 9A). The screw 64 engages a female interiorly threaded sleeve 66 formed in the head section 28 of handle 16, as shown in FIG. 8. In assembling the mirror 13 to the elongated handle 16, it is imperative that the mirror 13 be properly positioned to receive air and water from orifices 38, 40 and that it be properly aligned with the valve pushbuttons 46, 48. To ensure a proper alignment, the threading of the exteriorly threaded screw 64 has an elongated notch 68 that will line up with a handle notch 70, formed in the front face 74 of the head section 28, when the mirror 12 is properly aligned (see FIG. 7). Once the mirror 12 is rotated so that the notches 68, 70 are aligned, an interiorly threaded locking nut 72 is tightened down on the exposed threads of the exteriorly threaded screw 74 until the locking nut 72 is in tight face to face engagement with the front face 74 of the head section 28. The tightening down of the locking nut 72 insures that the proper positioning of the mirror 13 will be maintained. Thus, the threaded screw 64 si installed in the threaded sleeve 66 until the desired distance from the water orifice 40 and air orifices 38 to the reflective surface 12 is obtained. In the most preferred embodiment such distance is 10 to 35 millimeters. The alignment means provided by the screw notch 68 and handle notch 70 are then applied by rotating the screw 64 until the notches 68, 70 line up. Finally, the locking nut 72 is tightened down to prevent rotational translation of the mirror head 13 relative to the handle 16 or longitudinal translation within the sleeve 66. The mirror 12 is replaceable merely by loosening the locking nut 72 and unscrewing the screw 64 from the sleeve 66.

Figure 9B:
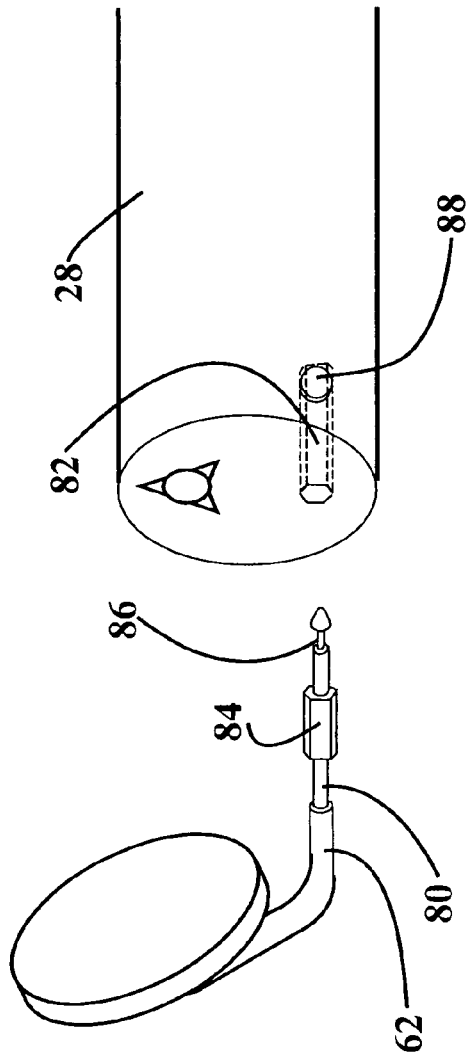
FIG. 9B is a detail view depicting the alignment provisions comprising a hexagonal shank and sleeve and locking device ensuring proper positioning of the reflective surface relative to the elongated handle and air and water orifices.

An alternative means for retaining the position of the mirror head 13 relative to the handle 16 is provided by a shank 80, extending from the angled arm 62, that is received in a sleeve 82 formed in the head section 28. At least a portion 84 of the shank 80 is geometrically shaped, with the sleeve 82 being correspondingly geometrically shaped to prevent rotational translation of the shank 80 within the sleeve 82. As shown in FIG. 9B, the geometric shape fo the portion 84 employed is hexagonal, but any other shapes (triangular, square, pentagonal, etc.) may be used without departing from the principles of the present invention.

The shank 80 shown in FIG. 9B further includes a recess 86. When the shank 80 is properly positioned within the sleeve 82, the recess 86 is engaged by a locking device 88. As shown in FIG. 9B, the locking device 88 comprises an Allen screw that is tightened down to engage the recess 86 in the shank 80, thereby preventing longitudinal translation of the shank 80 within the sleeve 82. Alternative locking devices, such as spring loaded bearings or locking collet fingers, are contemplated and may be used to engage the recess 86 to prevent longitudinal translation without departing from the principles of the present invention.

In addition to providing a replaceable mirror head 13, the present invention also provides a replaceable valve body section 30, and a pushbutton air valve 46 and pushbutton water valve 48 that are themselves individually replaceable, provisions designed and intended to make those items easily replaceable as set forth herein to improve the maintenance of the dental mirror 10.

As with any dental instrument, the mirror 10 of the present invention must be autoclavible, that is, it must be able to withstand sterilization through application of high heat and high pressure. To conform to such requirements, the mirror 10 is constructed wholly from non-corroding, non-pressure sensitive, non-heat sensitive materials. In the most preferred embodiment, the handle 16 and all metal parts are constructed from anodized aluminum. The O-rings that provide air and water tight seals around the valves and hose connections are made of VITON™.

The use of the inventive mirror 10 allows a dentist the luxury of having a reflective surface 12 that he can position during a procedure that, regardless of the amount of drilling and spraying employed or of debris created, never needs to be removed or wiped clean. The inventive mirror 10, connected to an air line 24 and water line 26, is held by the dentist in the same fashion as any other mirror would be except that his thumb pad will be positioned to engage air pushbutton valve 46 and water pushbutton valve 48. By depressing them individually or together, the dentist can remove debris and dry the reflective surface 12 without the mirror 10 ever leaving the patient's mouth.

The benefits of the present invention include time savings for all involved, dentist, staff and patient, because the time required to perform virtually every procedure will be reduced because there is no longer a need to continually remove a mirror, wipe it clean, reinsert it and get reoriented to the surgical site.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

We claim:

1. A self cleaning dental mirror comprising:
   an elongated handle;
   a reflective surface affixed to a first end of said elongated handle;
   means for communicating air through said elongated handle to at least one air orifice directing air at said reflective surface;

means for communicating water through said elongated handle to at least one water orifice directing water at said reflective surface;

an air valve means incorporated within said elongated handle for controlling air flow to said at least one air orifice directing air at said reflective surface; and a water valve means incorporated within said elongated handle for controlling water flow to said at least one water orifice directing water at said reflective surface;

wherein said air valve means and said water valve means comprise field replaceable pushbutton valves; and wherein said at least one air orifice and said at least one water orifice are arranged such that said at least one water orifice is encircled by multiple air orifices to disperse water as it is emitted from said at least one water orifice.

2. The self cleaning dental mirror of claim 1 further comprising means for removing and replacing said reflective surface and means for aligning said reflective surface with said field replaceable pushbutton valves, said means for aligning said reflective surface with said field replaceable valves being formed in said handle.

3. The self cleaning dental mirror of claim 1 further comprising a means for aligning the position of said reflective surface relative to said elongated handle such that said at least one air orifice and said at least one water orifice are directed at said reflective surface, wherein said means for aligning the position of said reflective surface to said elongated handle such that said at least one air orifice and said at least one water orifice are directed at said reflective surface is formed in said handle.

4. The self cleaning dental mirror of claim 3 wherein said means for aligning further comprises a means for locking the position of said reflective surface to prevent longitudinal translation relative to said elongated handle, wherein said locking means is formed in said handle.

5. The self cleaning dental mirror of claim 4 wherein said means for aligning comprises a geometrically shaped shank and a correspondingly geometrically shaped sleeve formed in said handle.

6. The self cleaning dental mirror of claim 5 wherein said means for locking holds said reflective surface is maintained a desired distance from said at least one water orifice and said at least one air orifice.

7. A self cleaning dental mirror comprising:
an elongated handle;
a reflective surface affixed to a first end of said elongated handle;
means for communicating air through said elongated handle to at least one air orifice directing air at said reflective surface;
means for communicating water through said elongated handle to at least one water orifice directing water at said reflective surface;
an air valve means incorporated within said elongated handle for controlling air flow to said at least one air orifice directing air at said reflective surface; and
a water valve means incorporated within said elongated handle for controlling water flow to said at least one water orifice directing water at said reflective surface;
wherein said air valve means and said water valve means comprise field replaceable pushbutton valves; and
wherein said means for communicating air and means for communicating water are concentric and extend the length of the handle to dispense water expelled from said at least one water orifice.

8. A self cleaning dental mirror comprising:
an elongated handle;
a reflective surface affixed to a first end of said elongated handle;
means for communicating air through said elongated handle to at least one air orifice directing air at said reflective surface;
means for communicating water through said elongated handle to at least one water orifice directing water at said reflective surface;
an air valve means incorporated within said elongated handle for controlling air flow to said at least one air orifice directing air at said reflective surface; and
a water valve means incorporated within said elongated handle for controlling water flow to said at least one water orifice directing water at said reflective surface;
wherein said air valve means and said water valve means comprise field replaceable pushbutton valves; and
wherein a water jet is surrounded by air jets.

9. A self cleaning dental mirror comprising:
an elongated handle;
a reflective surface affixed to a first end of said elongated handle;
means for communicating air through said elongated handle to at least one air orifice directing air at said reflective surface;
means for communicating water through said elongated handle to at least one water orifice directing water at said reflective surface;
an air valve means incorporated within said elongated handle for controlling air flow to said at least one air orifice directing air at said reflective surface; and
a water valve means incorporated within said elongated handle for controlling water flow to said at least one water orifice directing water at said reflective surface;
wherein said at least one air orifice and said at least one water orifice are arranged such that said at least one water orifice is encircled by multiple air orifices to disperse water as it is emitted from said at least one water orifice.

10. A self cleaning dental mirror comprising:
an elongated handle;
a reflective surface affixed to a first end of said elongated handle;
means for communicating air through said elongated handle to at least one air orifice directing air at said reflective surface;
means for communicating water through said elongated handle to at least one water orifice directing water at said reflective surface;
an air valve means incorporated within said elongated handle for controlling air flow to said at least one air orifice directing air at said reflective surface; and
a water valve means incorporated within said elongated handle for controlling water flow to said at least one water orifice directing water at said reflective surface;
wherein said means for communicating air and means for communicating water are concentric and extend the length of the handle to dispense water expelled from said at least one water orifice.

11. A self cleaning dental mirror comprising:
an elongated handle;
a reflective surface affixed to a first end of said elongated handle;
means for communicating air through said elongated handle to at least one air orifice directing air at said reflective surface;

means for communicating water through said elongated handle to at least one water orifice directing water at said reflective surface;

an air valve means incorporated within said elongated handle for controlling air flow to said at least one air orifice directing air at said reflective surface; and a water valve means incorporated within said elongated handle for controlling water flow to said at least one water orifice directing water at said reflective surface;

wherein a water jet is surrounded by air jets.

* * * * *